United States Patent [19]

Maeda et al.

[11] Patent Number: 4,923,450
[45] Date of Patent: May 8, 1990

[54] MEDICAL TUBES FOR PLACEMENT INTO THE BODY OF A PATIENT

[75] Inventors: Karo Maeda, Yokohama; Satoshi Ando, Osaka, both of Japan

[73] Assignee: Karo Maeda, Yokohama, Japan

[21] Appl. No.: 213,898

[22] Filed: Jun. 30, 1988

[30] Foreign Application Priority Data

Jul. 9, 1987 [JP] Japan .................. 62-171721

[51] Int. Cl.$^5$ ............................. A61M 5/325
[52] U.S. Cl. ..................... 604/265; 523/122
[58] Field of Search .......... 604/265; 523/122

[56] References Cited

U.S. PATENT DOCUMENTS 4,677,143 6/1987 Laurin et al. .

FOREIGN PATENT DOCUMENTS 3302567 7/1984 Fed. Rep. of Germany .
60181002 9/1989 Japan .
1582016 12/1980 United Kingdom .

OTHER PUBLICATIONS

Patent Abstracts of Japan Kokai-no. 60-181 002 (Kanebo K. K.).

Primary Examiner—John D. Yasko
Attorney, Agent, or Firm—Oblon, Spivak, McClelland, Maier & Neustadt

[57] ABSTRACT

Medical tubes such as a catheter or cannula having antibacterial action against *pseudomonas aeruginosa, staphylococcus aureus, escherichia coli* and fungus is disclosed.

Anhydrous or crystallization water containing powdered zeolite, wherein one or the whole of metals contained in said zeolite is substituted by at least one kind of ion exchangeable metals selected from the group consisting of Ag, Cu and Zn, is coated onto or kneaded into at least the portion of said tubes indwelled and placed into the body of a patient.

7 Claims, 1 Drawing Sheet

MEDICAL TUBES FOR PLACEMENT INTO THE BODY OF A PATIENT

FIELD OF THE INVENTION AND RELATED ART

1. Background of the Invention

The present invention relates to medical tubes placed into the body of a patient; and more particularly relates to medical tubes placed into the body of a patient such as a catheter or cannula having anti-bacterial action against *pseudomonas aeruginosa, staphylococcus aureus, escherichia coli* and fungus.

2. Discussion of the Background

Hitherto, medical tubes have been employed in placing the same into the body of a patient for a period of approximately two to seven days depending upon an object of its use. This is due to the fact that various bacilli are apt to generate about the circumference of a catheter thus placed so as to cause cystitis etc, for example. For the above reason, it was conventionally necessary to employ a newly sterilized catheter etc on occasion demands, which inevitably caused such inconvenience as giving pain to a patient or suffering from trouble ascribable to the replacement thereof.

Conventionally, a great variety of organometallic compounds or organic compounds was known as an anti-bacterial agents. However, those compounds have generally low melting points and also high volatility, thus rendering said compounds thermally unstable to the body heat so as to cause early deterioration of the effectiveness as an anti-bacterial agent in employing the same. Therefore, it was not suitable to employ such conventional anti-bacterial agent in a catheter etc.

On the other hand, as an anti-bacterial agent employed in the production of architectual products (e.g., on wall surfaces or building materials), anhydrous or water of crystallization containing powdered anti-bacterial compound comprising comprising one or the whole of metals contained in powdered zeolite being substituted by at least one kind of ion exchangeable metals selected from the group consisting of Ag, Cu and Zn was known as disclosed, for example, in Japanese patent laid-open publication No.181002/1985. However it was not clear as to whether or not the aforementioned anti-bacterial compound can be applicable to the field of medical care.

OBJECT AND SUMMARY OF THE INVENTION

With the above background in mind, the inventor of the present patent application has found after years of study that the aforementioned anti-bacterial compound can maintain anti-bacterial effect for a long period of time when said compound comes in touch with moisture or water.

It is an object of the present invention to provide medical tubes such as a catheter or cannula to be placed into the body of a patient having continuous anti-bacterial action for a long period of time.

Another object of the present invention is to provide medical tubes which are safe and further thermally stable to the body heat.

The aforementioned objects of the present invention can be attained by providing medical tubes for placement into the body of a patient comprising powdered zeolite wherein one portion or the whole of the metals contained in said zeolite is substituted by at least one kind of ion exchangeable metals selected from the group consisting of Ag,Cu and Zn being coated onto or kneaded into at least the portion of said medical tubes placed into the body of a patient.

As described above, according to the present invention, anhydrous or crystallization water containing powdered anti-bacterial compound obtainable by substituting one or the whole of metals contained in powdered zeolite by at least one kind of ion exchangeable metals selected from the group consisting of Ag,Cu and Zn is coated onto or kneaded at least into the portion of a catheter etc placed into the body; and therefore when said anti-bacterial compound comes in touch with secretion within the body, Ag ion, Cu ion or Zn ion is generated continuously for a long period of time so as to maintain the anti-bacterial effect to pseudomonas aeruginosa, staphylococcus aureus, escherichia coli and fungus, for example, because of its catalysis; and further said anti-bacterial compound is thermally stable to the body heat. Furthermore, said compound is safe for the body due to inorganic substance. Thus, it is possible to provide an effective medical tubes such as a catheter or cannula having anti-bacterial action against the aforementioned pseudomonas aeruginosa etc.

Figure 1:
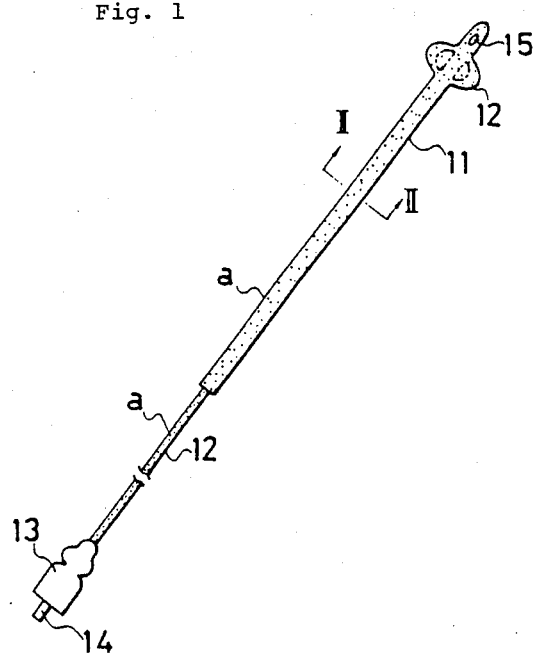
FIG. 1 to FIG. 2 show one embodiment according to the present invention, wherein the present invention is applied to a catheter to be placed into the urinary bladder.
Figure 2:
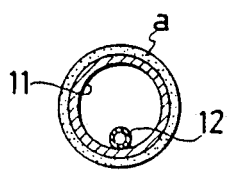

Among said Figures,

FIG. 1 is a perspective view of a catheter for catherization according to the present invention, and FIG. 2 is a sectional view taken along line II-II in FIG. 2.

DETAILED DESCRIPTION OF THE PREFERRED EMBODIMENTS

Hereinafter, embodiments according to the present invention will be described in detail with reference to the drawings. FIG. 1 to FIG. 2 are one embodiment according to the present invention in which the present invention is applied to a catheter for catherization for a long period of time. In the Figures,(a) is the anti-bacterial compound coated onto the portion of the catheter to be placed into the body of a patient and said compound is coated onto the outer and inner peripheral surfaces of a plastic tube as a cannula (11) by means of adhesives.

The aforementioned anti-bacterial compound is single substance of natural or synthetic anhydrous or crystallization water containing zeolite or the both, wherein one or the whole of metals contained said zeolite is substituted by at least one kind of ion exchangeable metals selected from the group consisting of Ag,Cu and Zn.

Said catheter itself is conventional and the catheter illustrated in the Figures is constituted in a manner that a discharging outlet (15) made of hard plastics is perforated at the front end of hard or semi plastic tube (11) and a plastic tube (12) with a smaller diameter than that of said tube (11) is disposed slidably free inside said tube (11) to be able to communicate with said outlet (15) at the end of the tube (12), and further an inlet (14) for charging liquid or air connecting to said tube (12) is mounted through a fitting (13) so as to place the same into the body of a patient. In FIG. 1, a balloon ( not illustrated ) disposed at the front end of said tube (12) is swelled by charging liquid or air thereinto.

As illustrated, the anti-bacterial compound (a) is coated onto a peripheral surface of the catheter according to the present invention. However, it is of course optional that said compound is coated onto the inner and outer surfaces of the tubes (11,12). Of course, it is further optional that said anti-bacterial compound is kneaded into moulding solution in moulding the aforementioned tubes.

Thickness (diameter) of the inhibit zone(mm.) against growth of *escherichia coli* and *staphylococcus aureus* by employing the anti-bacterial compound of the powdered zeolite according to the present invention was measured as shown in the following Table after 24 hrs. through a conventional experimental method.

| Kind of bacteria | Body fluid added | | |
|---|---|---|---|
| | Control | Urine | Serum |
| Escherichia coli | 5 | 5 | 4 |
| Staphylococcus aureus | 5 | 4 | 4 |

Note:
No body fluid is added to the Control and only the anti-bacterial compound of the powdered zeolite according to the present invention exists therein.

As is clear from the Table, the anti-bacterial effect against urine and serum can be well expected in employing the zeolite in a catheter; and the anti-bacterial action did not show deterioration continuously even after said zeolite came in touch with urine within the urinary bladder.

Thus, when the tubes(11,12) constituting a catheter onto which said anti-bacterial compound is coated or kneaded thereinto are placed into the body of a patient for a long period of time for the purpose of carrying out catheterization for the bed ridden or a paraplegic and also for discharging spodogenous matters collected within the peritoneal cavity out of the body in carrying out peritoneal dialysis, pseudomonas aeruginosa, staphylococcus aureus, escherichia coli and fungus will not generate about the circumference of the catheter thus placed into the body of the patient because of the anti-bacterial action of said anti-bacterial compound. Said anti-bacterial compound has strong anti-bacterial action particularly against pseudomonas aeruginosa. Furthermore, said compound has no toxicity. Of course, the present invention can be applied to various kinds of catheters or cannulas.

Thus, it becomes possible to extend considerably the placement time of the medical tubes according to the present invention compared to that of a conventional catheter or cannula, thereby lessening trouble ascribable to replacement thereof and at the same time alleviating the pain of a patient caused by said replacement.

Obviously, numerous modifications and variations of the present invention are possible in light of the above teachings. It is therefore to be understood that within the scope of the appended claims, the invention may be practiced otherwise than as specifically described herein.

What is claimed is:

1. A medical tube for placement into a patient comprising metal containing powdered zeolite, wherein at least one of the metals contained in said zeolite is substituted by at least one ion exchangeable metal selected from the group consisting of Ag, Cu and Zn, having anti-bacterial properties, the zeolite being coated onto or kneaded into said medical tube wherein said medical tube, when in contact with said patient, continuously exhibits said antibacterial properties of said ion exchangeable metal for a period of time of at least two days.

2. The medical tubes for placement into a patient according to claim 1, wherein said powdered zeolite is at least one member selected from the group consisting of natural zeolite and synthetic zeolite.

3. The medical tubes for placement into a patient according to claim 1, wherein said powdered zeolite is either coated onto at least one surface of the tube.

4. The medical tubes for placement into a patient according to claim 1, wherein said powdered zeolite is kneaded into said tubes.

5. The medical tubes for placement into a patient according to claim 1, wherein said medical tubes comprise a catheter.

6. The medical tubes for placement into a patient according to claim 1, wherein said medical tubes comprises a cannula.

7. The medical tubes for placement into a patient according to claim 1, wherein said powdered zeolite is anhydrous or a crystalline, hydrated zeolite having anti-bacterial action against *Pseudomonas eruginosa, Staphylococcus aureus, Escherichia coli* and fungus.

* * * * *